US00PP33190P2

(12) United States Plant Patent
Smit

(10) Patent No.: US PP33,190 P2
(45) Date of Patent: Jun. 22, 2021

(54) ***BEGONIA* PLANT NAMED 'EC-BEGO-2010'**

(50) Latin Name: *Begonia masoniana*
Varietal Denomination: EC-BEGO-2010

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/036,591

(22) Filed: Sep. 29, 2020

(51) Int. Cl.
*A01H 5/12* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 6/185
See application file for complete search history.

(56) References Cited

PUBLICATIONS

UPOV hit on *Begonia* plant named, 'EC-BEGO-2010', QZ PBR 20200914, filed Mar. 31, 2020.*

* cited by examiner

*Primary Examiner* — Anne Marie Grunberg
(74) *Attorney, Agent, or Firm* — Cassandra Bright

(57) ABSTRACT

A new and distinct cultivar of *Begonia masoniana* plant named 'EC-BEGO-2010' is disclosed, characterized by an upper leaf surface color of dark yellow-green. Foliage is large with long, thick petioles and distinctly hairy and puckered on the supper surface. The new variety is a *Begonia*, and is normally used as an ornamental garden or container plant.

2 Drawing Sheets

Figure 1:
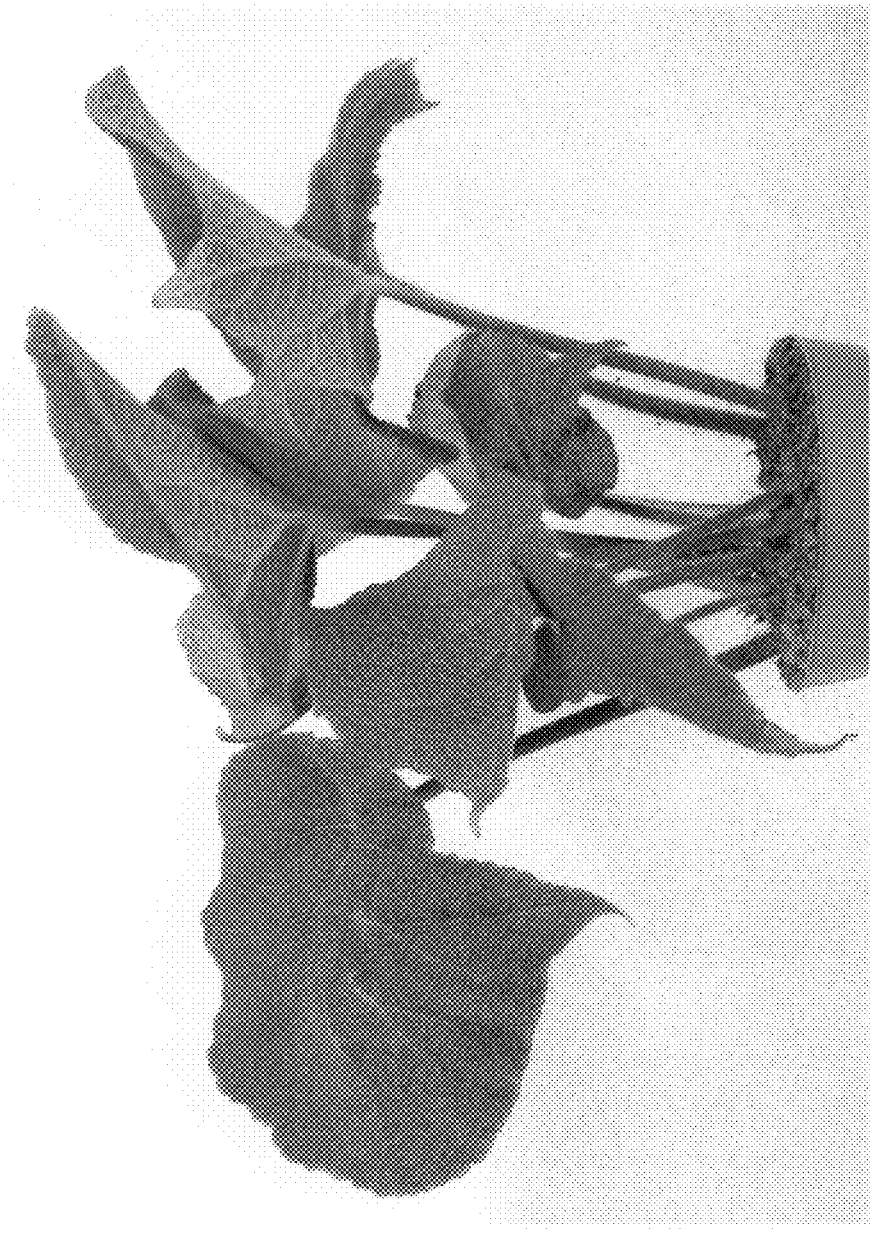

Latin name of the genus and species: *Begonia masoniana.*
Variety denomination: 'EC-BEGO-2010'.

BACKGROUND OF THE INVENTION

The new cultivar is the product of a planned breeding program. The new variety originated as the result of a crossing performed during 2014 of two proprietary, unpatented *Begonia masoniana* seedlings. The seed parent is the proprietary seedling referred to as "H". The pollen parent is the proprietary seedling referred to as "K". The selection of the new variety was made in 2017, by the inventor at a greenhouse located in Sappemeer, The Netherlands.

Asexual reproduction of the new cultivar 'EC-BEGO-2010' was first performed at a greenhouse in Sappemeer, The Netherlands by leaf cuttings during March 2017. 'EC-BEGO-2010' has since produced several generations and has shown that the unique features of this cultivar are stable and reproduced true to type.

SUMMARY OF THE INVENTION

The cultivar 'EC-BEGO-2010' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-2010'. These characteristics in combination distinguish 'EC-BEGO-2010' as a new and distinct *Begonia masoniana* cultivar:

1. Solid upper leaf surface color, dark yellow-green.
2. Distinct hairy/puckered leaf upper surface.
3. Large foliage with long, thick petioles.

PARENT COMPARISON

Plants of the new cultivar 'EC-BEGO-2010' are similar to plants of the seed parent variety in most horticultural characteristics. However, plants of the new cultivar 'EC-BEGO-2010' differ in the following:

1. The new variety has a larger plant habit than the seed parent.
2. The new variety has a longer petiole than the seed parent.
3. The new variety has larger foliage than the seed parent.

Plants of the new cultivar 'EC-BEGO-2010' are similar to plants of the pollen parent variety in most horticultural characteristics. However, plants of the new cultivar 'EC-BEGO-2010' differ in the following:

1. The new variety has solid green foliage pollen parent has brown foliage.
2. The new variety has longer petioles than the pollen parent.
3. The new variety is a larger plant than the pollen parent.

COMMERCIAL COMPARISON

Plants of the new cultivar 'EC-BEGO-2010' are similar to plants of the unpatented commercial variety, *Begonia* 'Iron Cross', in most horticultural characteristics. However, plants of the new cultivar 'EC-BEGO-2010' differ in the following:

1. The new variety has a solid leaf color, this comparator has a cross-shaped central splotch.

2. The new variety is a significantly larger plant than this comparator.
3. The new variety has larger leaves than this comparator.

Plants of the new cultivar 'EC-BEGO-2010' are similar to plants of the commercial variety, *Begonia maculata* 'EC-BEGO-1902', U.S. Plant Pat. No. 32,789 in most horticultural characteristics. However, plants of the new cultivar 'EC-BEGO-2010' differ in the following:

1. The new variety has solid colored leaves, while this comparator has a central splotch of radiating lines.
2. The new variety has solid colored foliage; this comparator has a different marginal coloration.

BRIEF DESCRIPTION OF THE PHOTOGRAPHS

The accompanying photograph in FIG. 1 illustrates in full color a typical plant of 'EC-BEGO-2010' grown in a greenhouse. The plant approximately 30 weeks of age.

Figure 2:
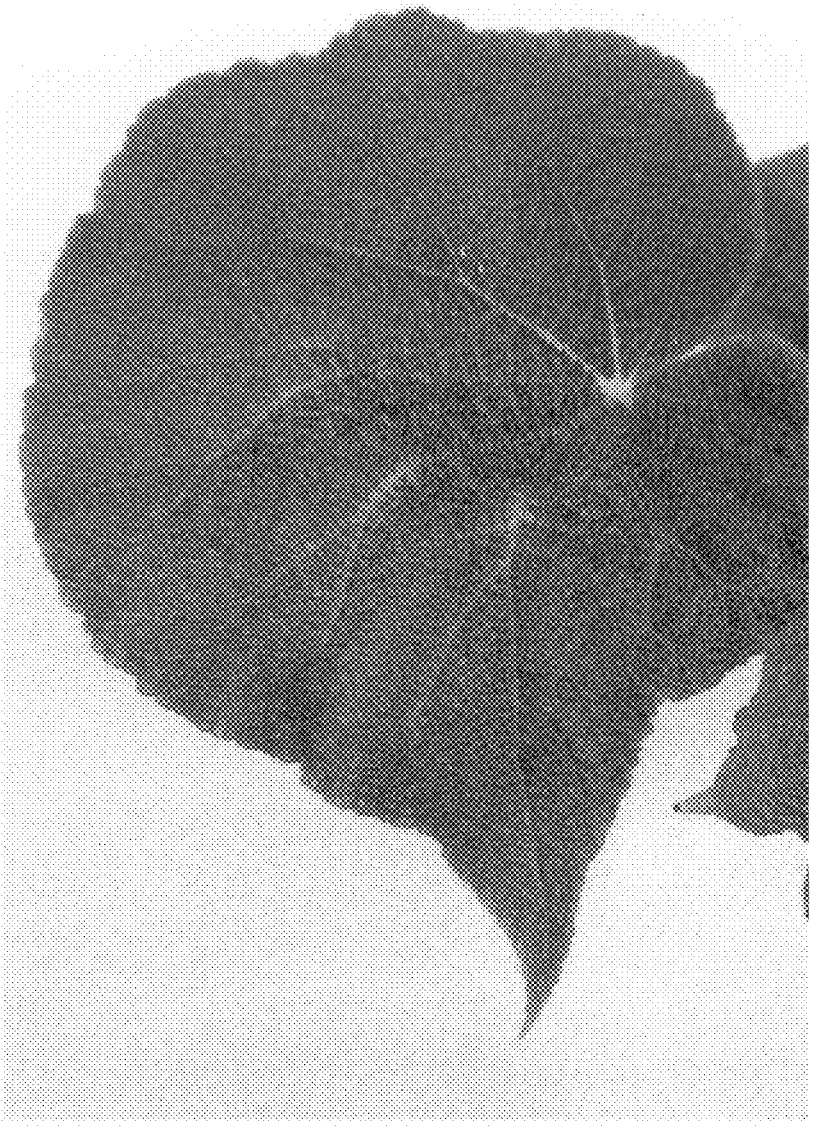

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 30-week-old 'EC-BEGO-2010' plants grown in September in a greenhouse in Sappemeer, The Netherlands. Measurements and numerical values represent averages of typical plant types.

Botanical classification: *Begonia masoniana* 'EC-BEGO-2010'.

Age of plant described: Approximately 30 weeks.

Container size: 14 cm.

PROPAGATION

Type of propagation typically used: Leaf cuttings.

Time to develop roots: About 15 days at approximately 21° C. in Summer.

Time to develop a rooted liner: About 70 days at approximately 21° C. in Summer.

Root description: Herbaceous, fine, moderately dense, freely branching. Brown in color, not accurately measured with R.H.S. chart.

PLANT

Plant type: Herbaceous perennial potted plant.

Growth habit: Flattened globular.

Height: 32.5 cm.

Plant spread: 37.8 cm.

Growth rate: Moderate.

Plant vigor: Moderate to high.

Branching characteristics: No branches; leaves grow directly from base.

FOLIAGE

*Arrangement*.—Alternate, single, basally emerging.

*Average length*.—Approximately 23.2 cm.

*Average width*.—Approximately 17.3 cm.

*Shape of blade*.—Broad ovate to near reniform.

*Apex*.—Long apiculate.

*Base*.—Oblique, lobes not overlapping, or very slightly overlapping.

*Margin*.—Irregular shallow crenate, finely undulate, densely covered with short strigose hairs, average length 1.0 mm, colored RHS Greyed-Purple 185D.

*Texture of top surface*.—Strongly papillose, on top of each papilla a single strigose hair is placed, average length: 1.0 mm, colored Greyed-Purple 185A.

*Texture of bottom surface*.—Densely covered with short hispid hairs, average length 1.0 mm. On main veins hairs colored Green-White 157A, hairs on lateral veins, colored greyed-red; 180D.

*Rugosity*.—Upper side: Somewhat rugose. Under side: Somewhat rugose.

*Luster*.—Upper side: Glossy. Under side: Matte.

*Color*.—Young foliage upper side: RHS Yellow-Green 144A. Tips of papillae Brown 200A. Young foliage under side: RHS Yellow-Green 146D, narrowly margined Greyed-Purple 183A. Mature foliage upper side: RHS Yellow-Green 146A, Upper section tinged 147A. Mature foliage under side: RHS Yellow-Green 148C, tinged Greyed-Red 182D.

*Venation*.—Type: Laciniate-reticulate. Venation color upper side: RHS Grey-Brown N199B. Venation color under side: RHS Yellow-Green 148C, tinged Greyed-Red 182D.

*Petiole*.—Length: Approximately 19.8 cm. Diameter: Approximately 9 mm. Color: Upper side: RHS Brown 200B. Under side: RHS Brown 200B. Texture: Densely pubescent with strigose hairs, average length 3.0 mm, colored RHS Greyed-Green 195D. Luster: Moderately glossy. Strength: Low.

FLOWER

Not observed to date.

REPRODUCTIVE ORGANS

Not observed to date.

OTHER CHARACTERISTICS

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

What is claimed is:

1. A new and distinct cultivar of *Begonia* plant named 'EC-BEGO-2010' as herein illustrated and described.

* * * * *